United States Patent
Wakita et al.

(10) Patent No.: US 7,803,942 B2
(45) Date of Patent: Sep. 28, 2010

(54) CRYSTALS OF MORPHINAN DERIVATIVE AND PROCESS FOR PRODUCING THE SAME

(75) Inventors: Hisanori Wakita, Kanagawa (JP); Masahiro Akimoto, Aichi (JP); Takahiro Takeda, Shizuoka (JP)

(73) Assignee: Toray Industries, Inc., Tokyo (JP)

( * ) Notice: Subject to any disclaimer, the term of this patent is extended or adjusted under 35 U.S.C. 154(b) by 559 days.

(21) Appl. No.: 11/887,842

(22) PCT Filed: Apr. 6, 2006

(86) PCT No.: PCT/JP2006/307331
§ 371 (c)(1), (2), (4) Date: Oct. 4, 2007

(87) PCT Pub. No.: WO2006/109671
PCT Pub. Date: Oct. 19, 2006

(65) Prior Publication Data
US 2009/0062544 A1    Mar. 5, 2009

(30) Foreign Application Priority Data
Apr. 6, 2005    (JP) ............... 2005-110096

(51) Int. Cl.
*C07D 489/08* (2006.01)
*C07D 489/00* (2006.01)

(52) U.S. Cl. .................. 546/44; 546/46; 546/45
(58) Field of Classification Search ............ 546/44, 546/45, 46
See application file for complete search history.

(56) References Cited

FOREIGN PATENT DOCUMENTS

| EP | 0 577 847 A1 | 1/1994 |
|----|--------------|--------|
| EP | 0 657 163 A1 | 6/1995 |
| EP | 0 661 283 A1 | 7/1995 |
| EP | 0 663 401 A1 | 7/1995 |
| EP | 0846694 A1 | 6/1998 |
| EP | 0 897 726 A1 | 2/1999 |
| WO | WO-93/15081 A1 | 8/1993 |
| WO | WO-95/01178 A1 | 1/1995 |
| WO | WO-95/03307 A1 | 2/1995 |
| WO | WO-95/03308 A1 | 2/1995 |
| WO | WO-98/23290 A1 | 6/1998 |

OTHER PUBLICATIONS

M.R. Caira, "Crystalline Polymorphism of Organic Compounds," Topics in Current Chemistry, vol. 198, Jan. 1, pp. 163-208, Springer, Berlin, DE, XP001156954, 1998.

Nagase, H. et al., Chem. Pharm. Bull., 1998, vol. 46, No. 2, pp. 366-369.

*Primary Examiner*—Charanjit S Aulakh
(74) *Attorney, Agent, or Firm*—Birch, Stewart, Kolasch & Birch, LLP (57) ABSTRACT

The present invention is directed to provide 17-cyclopropylmethyl-3,14β-dihydroxy-4,5α-epoxy-6β-[N-methyl-trans-3-(3-furyl)acrylamido]morphinan hydrochloride consistent in quality after production and having high purity. A crystal of 17-cyclopropylmethyl-3,14β-dihydroxy-4,5α-epoxy-6β-[N-methyl-trans-3-(3-furyl)acrylamido]morphinan hydrochloride including a A-form, B-form or C-form crystal thereof, and a process for producing the same are provided.

12 Claims, 8 Drawing Sheets

CRYSTALS OF MORPHINAN DERIVATIVE AND PROCESS FOR PRODUCING THE SAME

TECHNICAL FIELD

The present invention relates to a crystal of 17-cyclopropylmethyl-3,14β-dihydroxy-4,5α-epoxy-6β-[N-methyl-trans-3-(3-furyl)acrylamido]morphinan hydrochloride which has an analgesic, diuretic and antipruritic action and is useful as an active ingredient of analgesic, diuretic and antipruritic agents, and a process for producing the same.

BACKGROUND ART

17-Cyclopropylmethyl-3,14β-dihydroxy-4,5α-epoxy-6β-[N-methyl-trans-3-(3-furyl)acrylamido]morphinan hydrochloride represented by the following formula (I):

(I)

is described in patent document 1. This compound has been demonstrated to be a compound useful as an active ingredient of analgesic, diuretic and antipruritic agents. Patent document 1 specifically discloses the compound together with physiochemical properties thereof.

[Patent document 1]: JP Patent No. 2525552 (Example 68)

Figure 4:
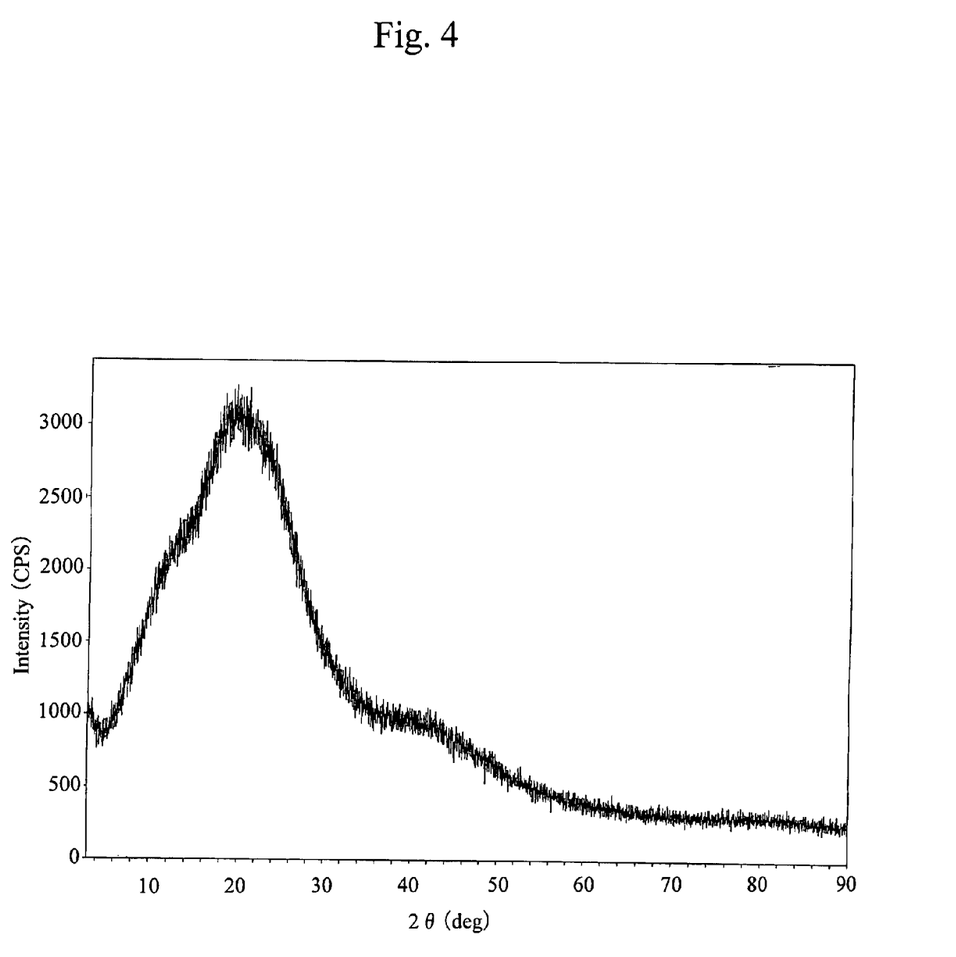
FIG. 4 is a powder X-ray diffraction pattern of the amorphous powder of 17-cyclopropylmethyl-3,14β-dihydroxy-4,5α-epoxy-6β-[N-methyl-trans-3-(3-furyl)acrylamido]morphinan hydrochloride disclosed in patent document 1.

During intensive studies on the physical properties of the compound represented by the above formula (I), the present inventors have found that whereas the compound (I) produced according to Example 68 in patent document 1 is amorphous as shown in FIG. 4, compound (I) has crystal polymorphism, i.e., is present as an A-form, B-form or C-form crystal as described later, when produced by a method different from the above method.

Generally, a compound having crystal polymorphism sometimes has physical properties different for each crystal. Particularly in the medicinal field, there are known to be differences in terms of solubility, solution velocity, stability, absorbability, or the like. Thus, it is possible that even use of the same compound provides no desired potency thereof or leads to a potency different from that predicted owing to a difference in crystal form, which causes unforeseen circumstances. For that reason, there is a need for the provision of the compound of consistent quality which can be expected to always have a constant potency.

Thus, when a compound having crystal polymorphism is used as a medicine, it is necessary to stably provide the compound having uniform crystal form in order to ensure the uniform quality and constant potency thereof.

The presence of a crystal of the compound represented by the above formula (I) has previously been quite unknown, and patent document 1 also does not describe or suggest the presence of a crystal or crystal polymorphism thereof.

Accordingly, the present inventors compared an amorphous form of compound (I) prepared according to Example 68 in patent document 1 with a crystal of compound (I) produced by a method different from the above method. As a result, it has been found that whereas the amorphous compound is not consistent in quality after production and has low purity, the crystal has no such problems and is excellent as an active ingredient of medicines or as a preparation for analyzing medicines.

DISCLOSURE OF THE INVENTION

The present invention encompasses the following invention.

(1) A crystal of 17-cyclopropylmethyl-3,14β-dihydroxy-4,5α-epoxy-6β-[N-methyl-trans-3-(3-furyl)acrylamido]morphinan hydrochloride.

(2) The crystal of the compound described in item (1) above, having highly intense diffraction peaks at the positions of 2θ of about 12.0°, about 18.9° and about 19.2° in a powder X-ray diffraction pattern thereof.

(3) The crystal of the compound described in item (1) above, having highly intense diffraction peaks at the positions of 2θ of about 7.6°, about 15.9° and about 18.5° in a powder X-ray diffraction pattern thereof.

(4) The crystal of the compound described in item (1) above, having highly intense diffraction peaks at the positions of 2θ of about 7.2°, about 17.2° and about 21.2° in a powder X-ray diffraction pattern thereof.

(5) A process for producing the crystal described in item (1) or (2) above, comprising reacting 17-cyclopropylmethyl-3,14β-dihydroxy-4,5α-epoxy-6β-[N-methyl-trans-3-(3-furyl)acrylamido]morphinan with hydrochloric acid in a good solvent, followed by mixing the reaction solution with a poor solvent and stirring the mixture.

(6) The process described in item (5) above, wherein the good solvent is methanol and the poor solvent is 2-propanol.

(7) A process for producing the crystal described in item (1) or (3) above, comprising reacting 17-cyclopropylmethyl-3,14β-dihydroxy-4,5α-epoxy-6β-[N-methyl-trans-3-(3-furyl)acrylamido]morphinan with hydrochloric acid in water, followed by leaving the reaction solution.

(8) A process for producing the crystal described in item (1) or (3) above, comprising reacting 17-cyclopropylmethyl-3,14β-dihydroxy-4,5α-epoxy-6β-[N-methyl-trans-3-(3-furyl)acrylamido]morphinan with hydrochloric acid in water, followed by adding ethanol to the reaction solution and then distilling off a part of the solvent under reduced pressure before leaving or stirring the residue.

(9) A process for producing the crystal described in any one of items (1) to (4) above, comprising recrystallizing 17-cyclopropylmethyl-3,14β-dihydroxy-4,5α-epoxy-6β-[N-methyl-trans-3-(3-furyl)acrylamido]morphinan hydrochloride in a solvent selected from the group consisting of methanol/2-propanol, ethanol/water, water and ethanol.

(10) A process for producing the crystal described in item (1) or (2) above, comprising recrystallizing, in methanol/2-propanol, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β-[N-methyl-trans-3-(3-furyl)acrylamido]morphinan with hydrochloric acid.

(11) A process for producing the crystal described in item (1) or (3) above, comprising recrystallizing, in ethanol/water or water, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β-[N-methyl-trans-3-(3-furyl)acrylamido]morphinan with hydrochloric acid.

(12) A process for producing the crystal described in item (1) or (4) above, comprising recrystallizing, in ethanol, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β-[N-methyl-trans-3-(3-furyl) acrylamido]morphinan with hydrochloric acid.

The crystal of the present invention is optimal as a medicine intended to be constant in the pH value of the product after production and to have consistent quality. The crystal also has an extremely low content of the cis isomer as the prime impurity and is high in purity.

BEST MODE FOR CARRYING OUT THE INVENTION

The present invention provides a crystal of the compound represented by the above formula (I).

The crystal of the present invention can be produced by any of processes described below.

<First Process>

17-Cyclopropylmethyl-3,14β-dihydroxy-4,5α-epoxy-6β-[N-methyl-trans-3-(3-furyl)acrylamido]morphinan (hereinafter, in some cases, referred to as "free morphinan derivative") is reacted with hydrochloric acid in a good solvent, followed by mixing the reaction solution with a poor solvent and stirring the mixture.

Examples of the good solvent include methanol, ethanol and n-propanol; preferred is methanol. Examples of the poor solvent include 2-propanol, 2-butanol, and t-butanol; preferred is 2-propanol.

The amount of the good solvent used for the reaction with hydrochloric acid is typically 2 to 100 mL, preferably 8 to 12 mL based on 1 g of the free morphinan derivative.

The hydrochloric acid is typically used at a concentration of 0.1 to 12 N, preferably 1 to 2 N. The amount of hydrochloric acid is typically 0.9 to 1.5 equivalents, preferably 1.0 to 1.1 equivalents.

The volume ratio of the good solvent to the poor solvent is typically 1 to 3:5, preferably 1.5 to 2.5:5.

After mixing with the poor solvent and stirring the mixture, a seed crystal is preferably added. Examples of the seed crystal used here include an A-form crystal or C-form crystal.

After adding the seed crystal, the mixture is typically stirred for 1 to 30 days, preferably 1 to 5 days. The stirring is performed at 0 to 30° C.

The treatment is carried out using methanol as the good solvent and 2-propanol as the poor solvent under the above conditions to provide an A-form crystal of the compound represented by the above formula (I), i.e., a crystal having highly intense diffraction peaks at the positions of 2θ of about 12.0°, about 18.9° and about 19.2° in a powder X-ray diffraction pattern thereof.

<Second Process>

The free morphinan derivative is reacted with hydrochloric acid in water, followed by leaving the reaction solution.

The amount of the water used as a solvent is typically 2 to 100 mL, preferably 6 to 8 mL based on 1 g of the free morphinan derivative.

The hydrochloric acid is typically used at a concentration of 0.1 to 12 N, preferably 1 to 2 N. The amount of hydrochloric acid is typically 0.9 to 1.5 equivalents, preferably 0.95 to 1.05 equivalents.

After adding the hydrochloric acid, a seed crystal may be optionally added. Examples of the seed crystal used here include a B-form crystal in Example 4.

After adding the hydrochloric acid and optionally the seed crystal, the mixture is typically left for 1 to 10 days, preferably 1 to 4 days.

The treatment is performed under the above conditions to provide a B-form crystal of the compound represented by the above formula (I), i.e., a crystal having highly intense diffraction peaks at the positions of 2θ of about 7.6°, about 15.9° and about 18.5° in a powder X-ray diffraction pattern thereof.

<Third Process>

The free morphinan derivative is reacted with hydrochloric acid in water, followed by adding ethanol to the reaction solution and then distilling off a part of the solvent under reduced pressure before leaving or stirring the residue.

The amount of the water used as a solvent is typically 1 to 100 mL, preferably 2 to 4 mL based on 1 g of the free morphinan derivative.

The hydrochloric acid is typically used at a concentration of 0.1 to 12 N, preferably 1 N. The amount of hydrochloric acid is typically 0.9 to 1.5 equivalents, preferably 0.95 to 1.05 equivalents.

The volume ratio of the water to the ethanol is typically 0.5 to 2:1, preferably 0.75 to 1.25:1.

After adding the ethanol, a part of the solvent is distilled off under reduced pressure; here, the concentration degree is typically 2 to 10 times, preferably 3 to 5 times.

Then, the residue is typically left for 1 to 30 days, preferably 1 to 10 days.

The treatment is performed under the above conditions to provide a B-form crystal of the compound represented by the above formula (I), i.e., a crystal having highly intense diffraction peaks at the positions of 2θ of about 7.6°, about 15.9° and about 18.5° in a powder X-ray diffraction pattern thereof.

<Fourth Process>

17-Cyclopropylmethyl-3,14β-dihydroxy-4,5α-epoxy-6β-[N-methyl-trans-3-(3-furyl)acrylamido]morphinan hydrochloride is recrystallized in a solvent selected from the group consisting of methanol/2-propanol, ethanol/water, water and ethanol.

The process for producing the 17-cyclopropylmethyl-3,14β-dihydroxy-4,5α-epoxy-6β-[N-methyl-trans-3-(3-furyl) acrylamido]morphinan hydrochloride used in the fourth process is not particularly limited; examples thereof include a process involving reacting the free morphinan derivative with hydrochloric acid.

The volume ratio of methanol to 2-propanol in the methanol/2-propanol used as a recrystallization solvent is typically 1 to 3:5, preferably 1.5 to 2.5:5. The volume ratio of ethanol to water in the ethanol/water used as a recrystallization solvent is typically 0.5 to 2:1, preferably 0.75 to 1.25:1.

The amount of the recrystallization solvent is typically 10 to 100 mL, preferably 30 to 40 mL based on 1 g of the hydrochloride.

The use of methanol/2-propanol as the recrystallization solvent provides the above A-form crystal; the use of ethanol/water or water provides the B-form crystal.

The use of ethanol as the recrystallization solvent also provides a C-form crystal of the compound represented by the above formula (I), i.e., a crystal having highly intense diffraction peaks at the positions of 2θ of about 7.2°, about 17.2° and about 21.2° in a powder X-ray diffraction pattern thereof.

The resultant crystals can be isolated by washing and drying by an ordinary method.

Figure 1:
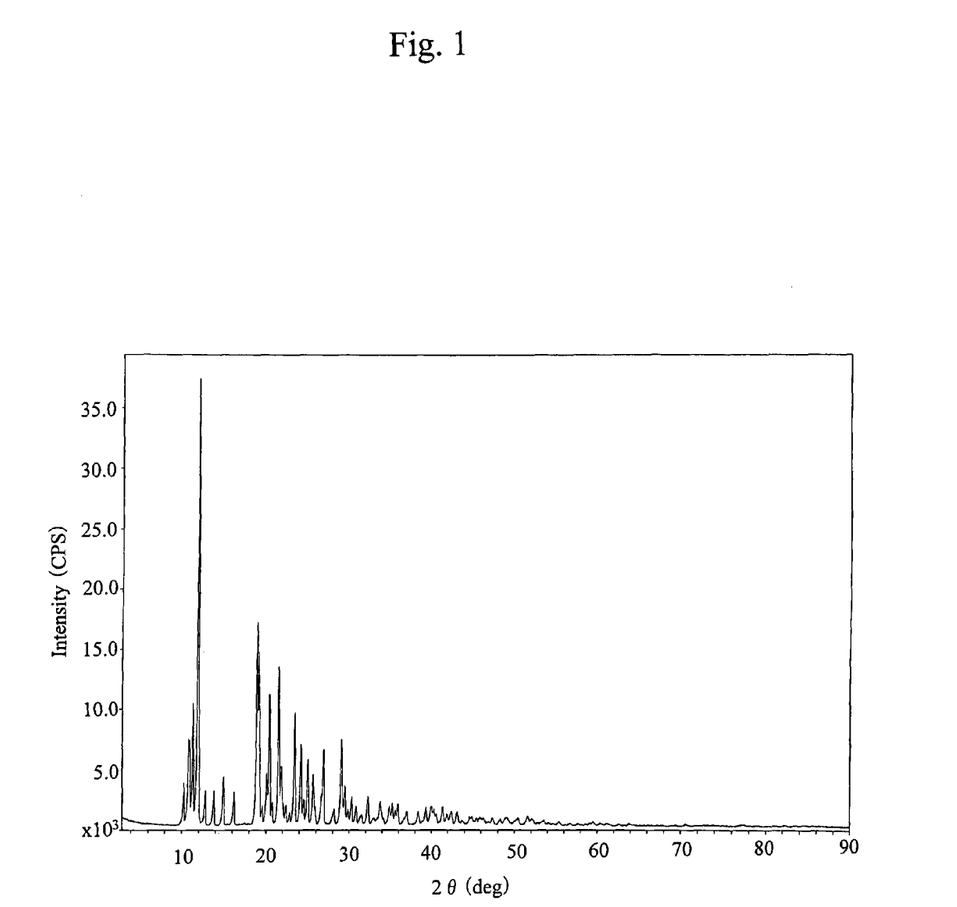
FIG. 1 is a powder X-ray diffraction pattern of an A-form crystal of 17-cyclopropylmethyl-3,14β-dihydroxy-4,5α-epoxy-6β-[N-methyl-trans-3-(3-furyl)acrylamido]morphinan hydrochloride.
Figure 2:
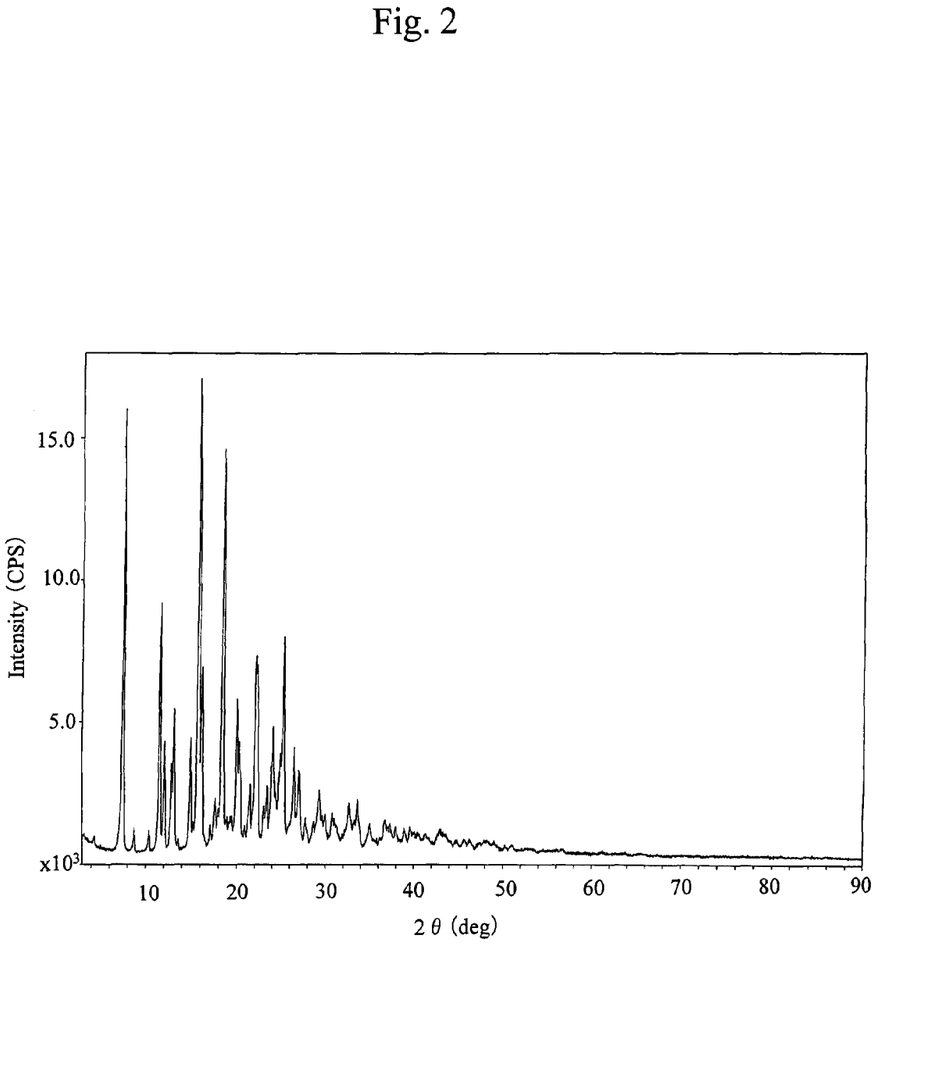
FIG. 2 is a powder X-ray diffraction pattern of a B-form crystal of 17-cyclopropylmethyl-3,14β-dihydroxy-4,5α-epoxy-6β-[N-methyl-trans-3-(3-furyl)acrylamido]morphinan hydrochloride.
Figure 3:
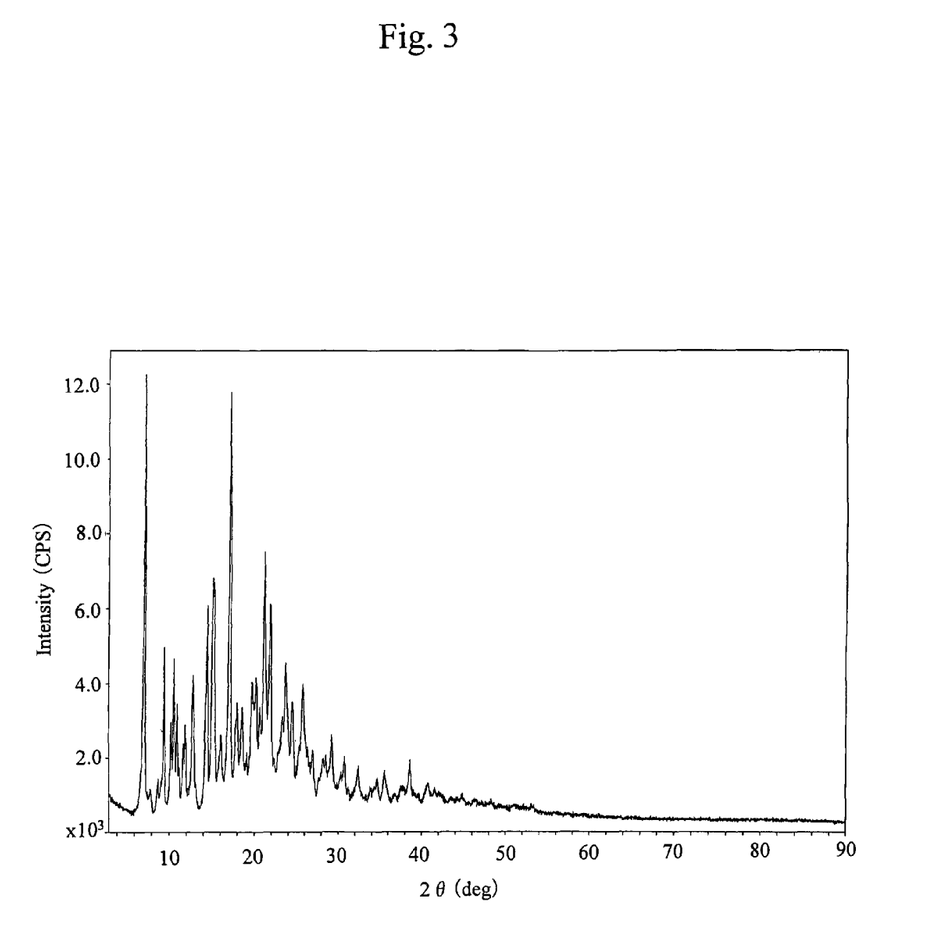
FIG. 3 is a powder X-ray diffraction pattern of a C-form crystal of 17-cyclopropylmethyl-3,14β-dihydroxy-4,5α-epoxy-6β-[N-methyl-trans-3-(3-furyl)acrylamido]morphinan hydrochloride.
Figure 5:
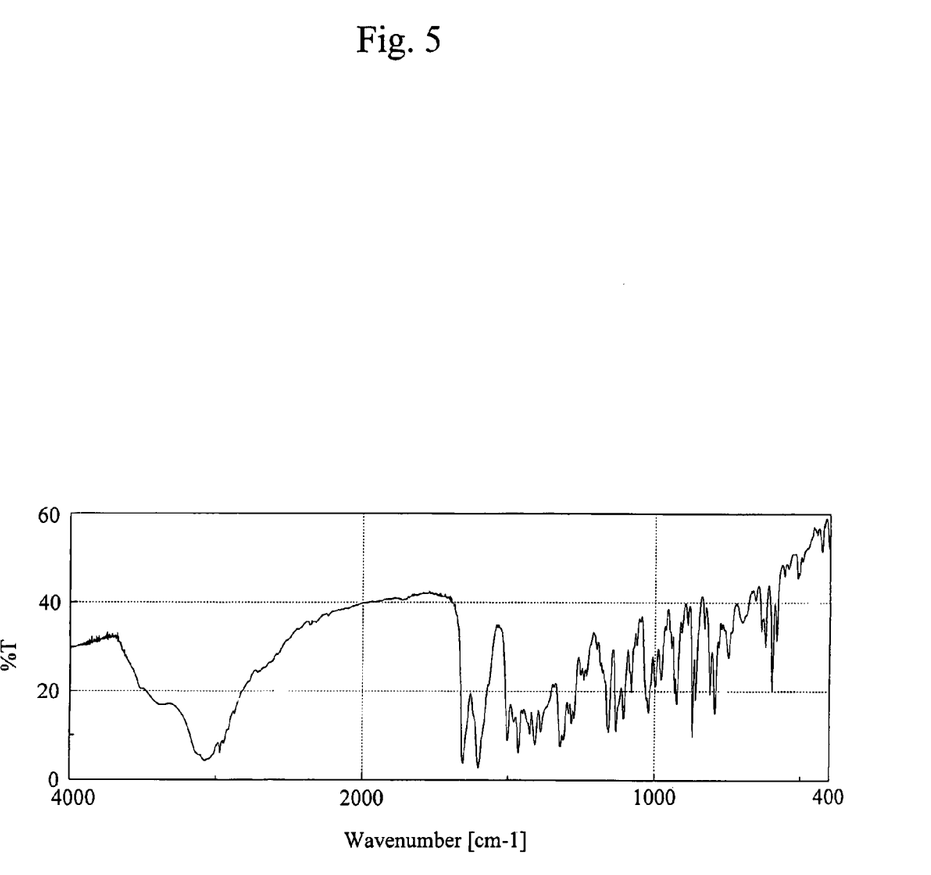
FIG. 5 is an infrared absorption spectrum of an A-form crystal of 17-cyclopropylmethyl-3,14β-dihydroxy-4,5α-epoxy-6β-[N-methyl-trans-3-(3-furyl)acrylamido]morphinan hydrochloride.
Figure 6:
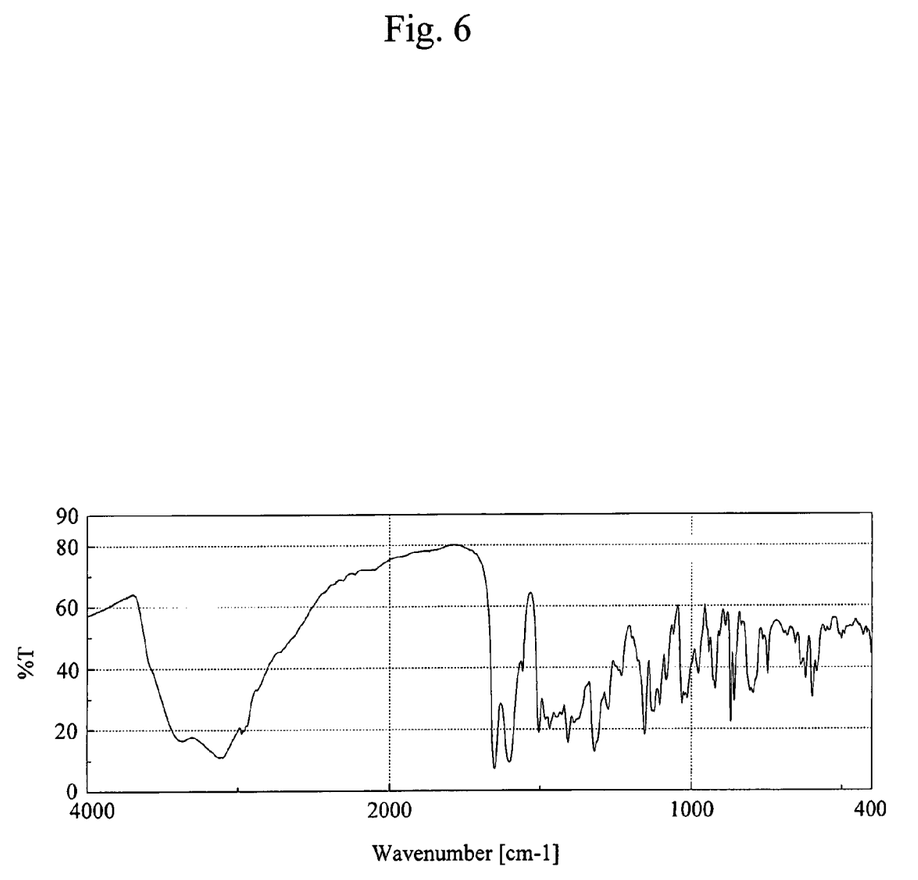
FIG. 6 is an infrared absorption spectrum of a B-form crystal of 17-cyclopropylmethyl-3,14β-dihydroxy-4,5α-epoxy-6β-[N-methyl-trans-3-(3-furyl)acrylamido]morphinan hydrochloride.
Figure 7:
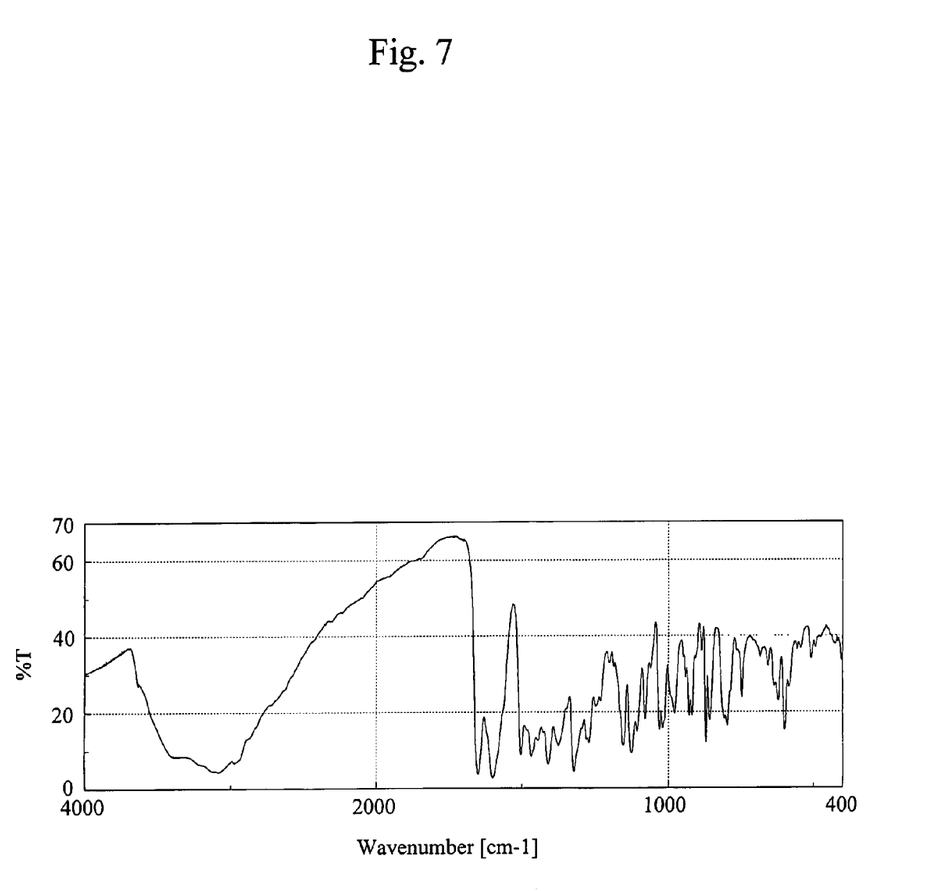
FIG. 7 is an infrared absorption spectrum of a C-form crystal of 17-cyclopropylmethyl-3,14β-dihydroxy-4,5α-epoxy-6β-[N-methyl-trans-3-(3-furyl)acrylamido]morphinan hydrochloride.

The A-form, B-form and C-form crystals of the present invention have substantially the same powder X-ray diffraction patterns as those shown in FIGS. 1, 2 and 3, respectively, and substantially the same infrared absorption spectrum as those depicted in FIGS. 5, 6 and 7, respectively.

Each spectral data should not be strictly interpreted since it can vary because of the nature thereof. By way of example, because of the nature of powder X-ray diffraction spectrum data, the diffraction angle 2θ and the overall pattern are important in qualifying the identity of crystals; the relative intensity can somewhat vary depending on the direction of crystal growth, the size of crystal particles and the conditions of measurement. In addition, the overall pattern is important in qualifying the identity of crystals also for infrared absorption spectrum data; the pattern can somewhat vary depending on the conditions of measurement. Thus, the crystal of the present invention includes that having a pattern totally similar to that of data of powder X-ray diffraction spectrum or infrared absorption spectrum of the crystal of the present invention.

This description includes part or all of the contents as disclosed in the description and/or drawings of Japanese Patent Application No. 2005-110096, which is a priority document of the present application.

EXAMPLES

The present invention is more specifically described below based on Examples. However, the invention is not intended to be limited to these Examples.

Reference Example 1

Amorphous Powder of Compound (I)

There was taken 2.02 g of 17-cyclopropylmethyl-3,14β-dihydroxy-4,5α-epoxy-6β-[N-methyl-trans-3-(3-furyl)acrylamido]morphinan, which was then suspended in 20 mL of ethanol, followed by adding 4.2 mL of 1 N hydrochloric acid before concentrating and drying the mixture to provide 2.34 g of an amorphous powder of the title compound.

Figure 8:
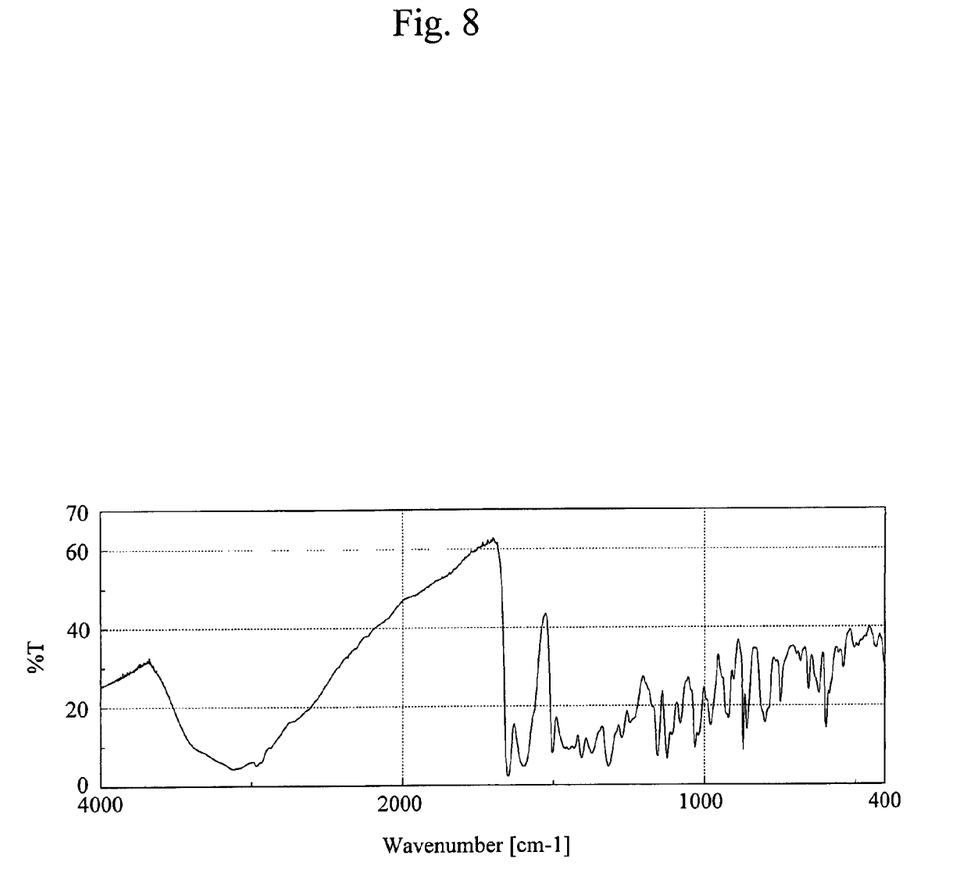
FIG. 8 is an infrared absorption spectrum of the amorphous powder of 17-cyclopropylmethyl-3,14β-dihydroxy-4,5α-epoxy-6β-[N-methyl-trans-3-(3-furyl)acrylamido]morphinan hydrochloride disclosed in patent document 1.

The infrared absorption spectrum thereof is shown in FIG. 8. The powder X-ray diffraction pattern thereof is shown in FIG. 4.

Reference Example 2

Amorphous Powder of Compound (I)

There was taken 3.00 g of 17-cyclopropylmethyl-3,14β-dihydroxy-4,5α-epoxy-6β-[N-methyl-trans-3-(3-furyl)acrylamido]morphinan, which was then suspended in 30 mL of ethanol, followed by adding 6.25 mL of 1 N hydrochloric acid before concentrating and drying the mixture to provide 3.45 g of an amorphous powder of the title compound. This compound had an infrared absorption spectrum agreeing with that of the compound obtained in Reference Example 1.

Reference Example 3

Amorphous Powder of Compound (I)

There was taken 2.01 g of 17-cyclopropylmethyl-3,14β-dihydroxy-4,5α-epoxy-6β-[N-methyl-trans-3-(3-furyl)acrylamido]morphinan, which was then suspended in 20 mL of ethanol, followed by adding 4.2 mL of 1 N hydrochloric acid before concentrating and drying the mixture to provide 2.31 g of an amorphous powder of the title compound. This compound had an infrared absorption spectrum agreeing with that of the compound obtained in Reference Example 1.

Example 1

A-Form Crystal of Compound (I)

There was taken 2.00 g of 17-cyclopropylmethyl-3,14β-dihydroxy-4,5α-epoxy-6β-[N-methyl-trans-3-(3-furyl)acrylamido]morphinan, which was then suspended in 20 mL of methanol, followed by adding 4.4 mL of 1 N hydrochloric acid before filtration. The filtrate was added to 50 mL of 2-propanol, which was then stirred. The C-form crystal in Example 7 or the A-form crystal in Example 2 or 3 was added as a seed crystal thereto, which was stirred for 5 days and then filtered, followed by drying the crystal at room temperature. As a result, 1.82 g of an A-form crystal of the title compound was obtained.

The infrared absorption spectrum thereof is shown in FIG. 5. The powder X-ray diffraction pattern thereof is shown in FIG. 1.

Example 2

A-Form Crystal of Compound (I)

There was taken 20.65 g of 17-cyclopropylmethyl-3,14β-dihydroxy-4,5α-epoxy-6β-[N-methyl-trans-3-(3-furyl)acrylamido]morphinan, which was then suspended in 200 mL of methanol, followed by adding 22.6 mL of 2 N hydrochloric acid before filtration. The filtrate was added to 500 mL of 2-propanol, which was then stirred. The C-form crystal in Example 7 or the A-form crystal in Example 1 or 3 was added as a seed crystal thereto, which was stirred overnight and then filtered, followed by drying the crystal at room temperature. As a result, 16.66 g of an A-form crystal of the title compound was obtained. This compound had a powder X-ray diffraction pattern and infrared absorption spectrum agreeing with those of the compound obtained in Example 1.

Example 3

A-Form Crystal of Compound (I)

There was taken 2.00 g of 17-cyclopropylmethyl-3,14β-dihydroxy-4,5α-epoxy-6β-[N-methyl-trans-3-(3-furyl)acrylamido]morphinan, which was then suspended in 20 mL of methanol, followed by adding 4.4 mL of 1 N hydrochloric acid before filtration. The filtrate was added to 50 mL of 2-propanol, which was then stirred. The C-form crystal in Example 7 or the A-form crystal in Example 1 or 2 was added as a seed crystal thereto, which was stirred overnight and then filtered, followed by drying the crystal at room temperature. As a result, 1.21 g of an A-form crystal of the title compound was obtained. This compound had an infrared absorption spectrum agreeing with that of the compound obtained in Example 1.

Example 4

B-Form Crystal of Compound (I)

There was taken 10.01 g of 17-cyclopropylmethyl-3,14β-dihydroxy-4,5α-epoxy-6β-[N-methyl-trans-3-(3-furyl)acrylamido]morphinan, which was then suspended in 79 mL of water, followed by adding 20.8 mL of 1 N hydrochloric acid. The mixture was left in the dark for 4 days; the resultant crystal was filtered and dried under reduced pressure at room temperature to 40° C. As a result, 6.87 g of a B-form crystal of the title compound was obtained.

The infrared absorption spectrum thereof is shown in FIG. 6. The powder X-ray diffraction pattern thereof is shown in FIG. 2.

Example 5

B-Form Crystal of Compound (I)

There was taken 2.01 g of 17-cyclopropylmethyl-3,14β-dihydroxy-4,5α-epoxy-6β-[N-methyl-trans-3-(3-furyl)acrylamido]morphinan, which was then suspended in 14 mL of water, followed by adding 4.2 mL of 1 N hydrochloric acid. The B-form crystal in Example 4 or 6 was added as a seed crystal thereto, which was then left in the dark for 3 days; the resultant crystal was filtered and dried under reduced pressure at room temperature to 40° C. As a result, 0.61 g of a B-form crystal of the title compound was obtained. This compound had an infrared absorption spectrum agreeing with that of the compound obtained in Example 4.

Example 6

B-Form Crystal of Compound (I)

There was taken 2.01 g of 17-cyclopropylmethyl-3,14β-dihydroxy-4,5α-epoxy-6β-[N-methyl-trans-3-(3-furyl)acrylamido]morphinan, which was then suspended in 5.8 mL of water, followed by adding 4.2 mL of 1 N hydrochloric acid. To the resultant solution was added 10 mL of ethanol, which was then concentrated under reduced pressure until the weight of the solution was 6.3 g. The concentrate was left in a refrigerator for 8 days; the resultant crystal was then filtered and dried under reduced pressure at room temperature. As a result, 1.67 g of a B-form crystal of the title compound was obtained. This compound had a powder X-ray diffraction pattern and an infrared absorption spectrum agreeing with those of the compound obtained in Example 4.

Example 7

C-Form Crystal of Compound (I)

There was taken 2.02 g of 17-cyclopropylmethyl-3,14β-dihydroxy-4,5α-epoxy-6β-[N-methyl-trans-3-(3-furyl)acrylamido]morphinan, which was then suspended in 100 mL of ethanol, followed by adding 4.2 mL of 1 N hydrochloric acid. The resultant solution was concentrated under reduced pressure and dried to provide a solid. Thereto was added 200 mL of ethanol, which was dissolved by warming at 40 to 50° C., followed by concentrating the solution under reduced pressure so that the weight thereof was 17.31 g after the concentration. The concentrate was left in the dark for 12 days; the resultant crystal was filtered and dried at room temperature. As a result, 1.92 g of a C-form crystal of the title compound was obtained.

The infrared absorption spectrum thereof is shown in FIG. 7. The powder X-ray diffraction pattern thereof is shown in FIG. 3.

Example 8

C-Form Crystal of Compound (I)

There was taken 2.00 g of 17-cyclopropylmethyl-3,14β-dihydroxy-4,5α-epoxy-6β-[N-methyl-trans-3-(3-furyl)acrylamido]morphinan, which was then suspended in 100 mL of ethanol, followed by adding 4.2 mL of 1 N hydrochloric acid. The resultant solution was concentrated under reduced pressure and dried to provide a solid. Thereto was added 200 mL of ethanol, which was dissolved by warming at 40 to 50° C., followed by concentrating the solution under reduced pressure so that the weight thereof was 17.31 g after the concentration. The C-form crystal in Example 7 was added as a seed crystal thereto, which was left in the dark for 4 days; the resultant crystal was filtered and dried at room temperature. As a result, 1.77 g of a C-form crystal of the title compound was obtained. This compound had an infrared absorption spectrum agreeing with that of the compound obtained in Example 7.

Test Example 1

The amorphous powder obtained in Reference Example 3 and the crystals obtained in Examples 2, 5 and 8 were measured for purity using high performance liquid chromatography (HPLC).

Column: YMC-Pack ODS-AM-303

Mobile phase: solution A: 50 mmol/L—sodium dihydrogenphosphate aqueous solution, solution B: 50 mmol/L—sodium dihydrogenphosphate aqueous solution/acetonitrile=60/40 (v/v)

Composition of solution B in the mobile phase: 0 to 30 min.: 0→50%, 30 to 75 min.: 50→100%, 75 to 90 min.: 100%, 90 to 120 min.: 0%

Flow rate: 1 mL/min.

Column temperature: 40° C.

UV: 210 nm

As shown in Table 1, the crystals of 17-cyclopropylmethyl-3,14β-dihydroxy-4,5α-epoxy-6β-[N-methyl-trans-3-(3-furyl)acrylamido]morphinan hydrochloride of the present invention had high purity because of their extremely low contents of the cis isomer (17-cyclopropylmethyl-3,14β-dihydroxy-4,5α-epoxy-6β-[N-methyl-cis-3-(3-furyl)acrylamido]morphinan) as the prime impurity contained in the compound.

TABLE 1

Content of Cis Isomer Contained in Compound

| Compound | Content of Cis Isomer |
|---|---|
| Free-form | 0.12% |
| Hydrochloride (Amorphous Powder Obtained in Reference Example 3) | 0.13% |
| Hydrochloride (A-form Crystal Obtained in Example 2) | 0.05% |
| Hydrochloride (B-form Crystal Obtained in Example 5) | 0.03% |
| Hydrochloride (C-form Crystal Obtained in Example 8) | 0.09% |

Test Example 2

There was taken 100 mg each of the amorphous powders obtained in Reference Examples 1 to 3 and the A-form crystals obtained in Examples 1 to 3, to which 10 mL of decarbonated water was added for dissolution, followed by measuring the pH. The results are shown in Table 2.

TABLE 2 pH Reproducibility after Production

| | Compound | pH |
|---|---|---|
| Amorphous Powder | Reference Example 1 | 3.7 |
| | Reference Example 2 | 4.7 |
| | Reference Example 3 | 3.5 |
| A-form Crystal | Example 1 | 5.8 |
| | Example 2 | 5.4 |
| | Example 3 | 5.6 |

Whereas the amorphous powder of 17-cyclopropylmethyl-3,14β-dihydroxy-4,5α-epoxy-6β-[N-methyl-trans-3-(3-furyl)acrylamido]morphinan hydrochloride had no reproducibility in the pH after production, the A-form crystal of the present invention had a constant pH value, which is very useful for achieving consistent quality.

All publications, patents, and patent applications cited in this application are intended to be incorporated herein by reference in their entirety.

INDUSTRIAL APPLICABILITY

The present invention is utilized in the medicinal field.

The invention claimed is:

1. An A-form, B-form or C-form crystal of 17-cyclopropylmethyl-3,14β-dihydroxy-4,5α-epoxy-6β-[N-methyl-trans-3-(3-furyl)acrylamido]morphinan hydrochloride.

2. The crystal of the compound according to claim 1, having highly intense diffraction peaks at the positions of 2θ of about 12.0°, about 18.9° and about 19.2° in a powder X-ray diffraction pattern thereof.

3. The crystal of the compound according to claim 1, having highly intense diffraction peaks at the positions of 2θ of about 7.6°, about 15.9° and about 18.5° in a powder X-ray diffraction pattern thereof.

4. The crystal of the compound according to claim 1, having highly intense diffraction peaks at the positions of 2θ of about 7.2°, about 17.2° and about 21.2° in a powder X-ray diffraction pattern thereof.

5. A process for producing the crystal according to claim 1, comprising reacting 17-cyclopropylmethyl-3,14β-dihydroxy-4,5α-epoxy-6β-[N-methyl-trans-3-(3-furyl)acrylamido]morphinan with hydrochloric acid in a good solvent, followed by mixing the reaction solution with a poor solvent and stirring the mixture.

6. The process according to claim 5, wherein the good solvent is methanol and the poor solvent is 2-propanol.

7. A process for producing the crystal according to claim 1, comprising reacting 17-cyclopropylmethyl-3,14β-dihydroxy-4,5α-epoxy-6β-[N-methyl-trans-3-(3-furyl)acrylamido]morphinan with hydrochloric acid in water, followed by leaving the reaction solution.

8. A process for producing the crystal according to claim 1, comprising reacting 17-cyclopropylmethyl-3,14β-dihydroxy-4,5α-epoxy-6β[N-methyl-trans-3-(3-furyl)acrylamido]morphinan with hydrochloric acid in water, followed by adding ethanol to the reaction solution and then distilling off a part of the solvent under reduced pressure before leaving or stirring the residue.

9. A process for producing the crystal according to claim 1, comprising recrystallizing 17-cyclopropylmethyl-3,14β-dihydroxy-4,5α-epoxy-6β[N-methyl-trans-3-(3-furyl)acrylamido]morphinan hydrochloride in a solvent selected from the group consisting of methanol/2-propanol, ethanol/water, water and ethanol.

10. A process for producing the crystal according to claim 1, comprising recrystallizing, in methanol/2-propanol, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β[N-methyl-trans-3-(3-furyl)acrylamido]morphinan with hydrochloric acid.

11. A process for producing the crystal according to claim 1, comprising recrystallizing, in ethanol/water or water, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β-[N-methyl-trans-3-(3-furyl)acrylamido]morphinan with hydrochloric acid.

12. A process for producing the crystal according to claim 1, comprising recrystallizing, in ethanol, 17-cyclopropylmethyl-3,14β-dihydroxy-4,5α-epoxy-6β-[N-methyl-trans-3-(3-furyl)acrylamido]morphinan hydrochloride obtained by reacting 17-cyclopropylmethyl-3,14β-dihydroxy-4,5α-epoxy-6β-[N-methyl-trans-3-(3-furyl)acrylamido]morphinan with hydrochloric acid.

* * * * *